(12) United States Patent
van Duijn et al.

(10) Patent No.: US 6,762,293 B2
(45) Date of Patent: Jul. 13, 2004

(54) DIAGNOSTICS AND THERAPEUTICS FOR AUTOSOMAL DOMINANT HEMOCHROMATOSIS

(75) Inventors: Cock M. van Duijn, Rotterdam (NL); Peter Heutink, Rotterdam (NL); Ben A. Oostra, Bergschenhoek (NL)

(73) Assignee: Erasmus University Rotterdam, Rotterdam (NL)

( * ) Notice: Subject to any disclaimer, the term of this patent is extended or adjusted under 35 U.S.C. 154(b) by 0 days.

(21) Appl. No.: 09/973,180

(22) Filed: Oct. 10, 2001

(65) Prior Publication Data

US 2003/0082553 A1 May 1, 2003

Related U.S. Application Data

(60) Provisional application No. 60/301,429, filed on Jun. 29, 2001.

(51) Int. Cl.[7] .............................. C07H 21/04; C12Q 1/68
(52) U.S. Cl. .......................... 536/23.1; 536/24.3; 435/6; 435/91.1; 435/91.2
(58) Field of Search ............................... 536/23.1, 24.3; 435/6

(56) References Cited

U.S. PATENT DOCUMENTS

| | | | |
|---|---|---|---|
| 5,474,796 A | * | 12/1995 | Brennan .................... 427/2.13 |
| 5,674,681 A | | 10/1997 | Rothenberg |
| 5,705,343 A | | 1/1998 | Drayna et al. |
| 5,712,098 A | | 1/1998 | Tsuchihashi et al. |
| 5,753,438 A | | 5/1998 | Drayna et al. |
| 6,025,130 A | | 2/2000 | Thomas et al. |
| 6,140,305 A | | 10/2000 | Thomas et al. |

OTHER PUBLICATIONS

Montosi et al. "Autosomal–dominant hemochromaosis is associated with a mutation in the ferroportin (SLC11A3) gene." J. of Clinical Investigation, vol. 108, No. 4, pp. 619–623, Aug. 2001.*

Devalia et al. "Autosomal dominant reticuloendothelial iron overload associated with a 3–base pair deletion in the ferroportin 1 gene (SLC11A3)." Blood. vol. 100, No. 2, pp. 695–697, Jul 15, 2002.*

McKie et al. Genbank Accession No. AF231121. "Homo sapiens iron–regulated transporter IREG1 (IREG1)," Mar. 20, 2000.*

Olivier et al. Genbank Accession No. G11389. "Homo sapiens STS genomic." Mar. 30, 2000.*

Boehringer Mannheim. 1997 Biochemicals Catalog. p. 95.*

Hoefslott, Lies, et al., Characterization of the human lysosomal glucosidase gene, Biochem. J., 272, pp. 493–497 (1990).

Donovan, Adriana et al., "Positional cloning of zebrafish ferrportinl identifies a conserved vertebrate iron exporter," Nature Lett., 403, pp. 776 781 (2000).

Pietrangelo, Antonello et al., "Hereditary Hemochromatosis in Adults Without Pathogenic Mutations in the Hemochromatosis Gene", N.E. J. Med., 341(10), pp. 725–732 (1999).

Kato et al., "A Mutation in H–Perritin mRNA", Am. J. Hum. Genet., 69, p. 191 (2001).

* cited by examiner

Primary Examiner—W. Gary Jones
Assistant Examiner—Jeanine Goldberg
(74) Attorney, Agent, or Firm—Nath & Associates PLLC; Todd L. Juneau

(57) ABSTRACT

This invention relates generally to the gene, and mutations, that are responsible for the disease hemochromatosis (HH). In particular, the present invention provides for the presence of one or more mutations on the ferroportin 1 (SLC11A3) gene which results in aberrant SLC11A3 mediated iron transport. The invention also relates to methods for diagnostic tools, drugs and therapies developed for the treatment of patients with HH or anemia.

6 Claims, No Drawings

DIAGNOSTICS AND THERAPEUTICS FOR AUTOSOMAL DOMINANT HEMOCHROMATOSIS

This application claims benefit of U.S. Provisional Patent Application Serial No. 60/301,429 filed Jun. 29, 2001.

BACKGROUND OF THE INVENTION

1. Field of the Invention

The present invention relates generally to the gene, and mutations, that are responsible for the disease hemochromatosis (MIM604653). In particular, the present invention provides for the presence of one or more mutations on the SLC11A3 gene which results in aberrant SLC11A3 mediated iron transport. The invention also relates to methods for screening for HH and to HH diagnosis, prenatal screening and diagnosis, and therapies of HH disease, including gene therapeutics, protein and antibody based therapeutics, and small molecule therapeutics. The invention further relates to drugs and therapies developed for the treatment of patients with HH or anemia.

2. Description of the Related Art

Over the years, several known genes involved in iron metabolism have been implicated in the pathology of HH. However, not all instances of HH patients can be explained by mutations in these genes. In particular, it is known that approximately 60–85% of all instances of HH in adult patients are indicated by homozygosity for the C282Y mutation in the HLA-H/HFE gene on Chromosome 6p. Compound heterozygosity accounts for an additional 10% of cases. It is also known that a form of juvenile hemochromatosis maps to chromosome 1q and that a single family was found with a mutation in a transferrin receptor gene (TFR2) on chromosome 7q. However, the remaining 5–15% of patients indicated with HH do not possess any mutations on the known genes. For example, Kato et al., describe a heterzygous A49T mutation in the 5_UTR of the H-subunit of ferritin without specifically delineating the contributions of this gene to the HH disease state (Am. J. Human Genetics 69: 191–7 (2001)). Clearly, neither the precise physiological mechanism of iron overaccumulation nor every gene which is defective in this disease has been described.

Hemochromatosis is an inherited disorder of iron metabolism wherein the body accumulates excess iron. In symptomatic individuals, excess iron is deposited in a variety of organs which leads to organ failure. Disease states such as cirrhosis, diabetes, sterility, and other serious illnesses occur as a result. It has also been discovered that HH can be inherited by a dominant or pseudo-dominant mode of inheritance. Heretofore, HH was believed to be inherited solely as a recessive trait. In particular, the prior art limits HH to patients having homozygotes carrying two defective copies of the gene.

Hemochromatosis is also one of the most common genetic disorders. The prior art estimates that approximately 10% of individuals of Western European descent carry one copy of the HH gene mutation and that there are about one million homozygotes in the United States. HH, thus, represents one of the most common genetic disease mutations in individuals of Western European descent. Although HH ultimately produces debilitating symptoms, the majority of carriers have not been diagnosed. Indeed, it has been estimated that no more than a small fraction of affected individuals in the United States have been diagnosed with this condition.

Current diagnostic methods fail to comprehensively test for HH in individuals who are at risk, especially those individuals who are presymptomatic. Although blood iron parameters can be used as a screening tool, a confirmed diagnosis often employs a costly, invasive and high risk liver biopsy. An additional problem is that symptoms of HH are similar to those of other conditions and the severe effects of the disease tend not to appear immediately. Thus, there is a clear need for the development of an inexpensive and noninvasive comprehensive diagnostic test for detection of HH in order to facilitate comprehensive diagnosis and to provide comprehensive presymptomatic detection for the identification of HH carriers. Accordingly, comprehensive methods to identify persons who may be destined to become symptomatic in order to intervene in time to prevent excessive tissue damage associated with iron overload are desirable.

U.S. Pat. No. 6,025,130 ("Thomas et al.") describes a gene indicated for HH in the HLA region of Chromosome 6. Although Thomas et al. discloses a gene thought to cause HH, it does not provide for the remaining population of individuals who are symptomatic of HH but do not carry the mutation as taught by Thomas et al.

In the search for additional genes indicated for HH, one study generally concluded that HH can occur in adults who do not have pathogenic mutations in the hemochromatosis gene. See *N Engl J Med* 341:725–32 (1999). In particular, the study found that members of a single family of Italian descent displayed symptoms of one or more distinct genetic diseases that cause a type of adult hereditary iron overload which was not associated with the known HH gene. The study, however, failed to provide for the gene hypothesized to cause the disease.

Another study relating to Zebrafish concluded that the gene ferroportin 1 (FNP1) may be involved in mammalian disorders of iron deficiency or overload. *Nature*, 403:17 (2000). In particular, the study focused on hypochromia caused by inadequate circulatory iron levels in embryonic Zebrafish. The study found that two independent autosomal recessive mutations caused hypochromia in the Zebrafish embryo. Mammalian homologues of these genes include SLC11A3.

However, the transversion site disclosed by the study differs from the present invention and is not believed to be responsible for HH. In particular, the study specifically teaches that a C-to-A transversion at codon 361 prematurely terminates translation of the SLC11A3 gene and that a G-to-T transversion at an undisclosed location results in a single amino acid change from Leucine to Phenylalanine. Additionally, the study fails to explain how the amino acid change affects the SLC11A3 protein. Accordingly, the study does not provide any motivation or suggestion to one of ordinary skill in the art to believe that a C-to-A transversion at codon 361 or a G-to-T transversion at an undisclosed location causes about 5–15% of all HH cases.

Genetic markers are also known for a mutation in recessive hemochromatosis. Diagnostic methods and kits for its determination are disclosed by U.S. Pat. Nos. 5,753,438 and 5,705,343.

U.S. Pat. No. 5,712,098 ("Tsuchibashi et al.") also discloses recessive hereditary hemochromatosis diagnostic markers and diagnostic methods for same.

U.S. Pat. No. 5,674,681 ("Rothenberg") discloses a method for identifying an individual having or predisposed to having hemochromatosis by detecting a mutation in the gene encoding a nonclassical MHC class I heavy chain. Rothenberg also discloses methods for treating recessive hemochromatosis involving administration of a "leczyme"

having similar specificity for a carbohydrate ligand as the leczyme involved in the disease state. Clearly, the prior art fails to provide for the remaining 5–15% of patients indicated with HH who do not possess any mutations of known genes.

Accordingly, it would be highly desirable to identify, isolate, clone, and sequence the gene responsible for the remaining 5–15% of patients indicated with HH who do not possess any mutations of known genes. Such identification, isolation, cloning, and sequencing of the gene would enable the design and manufacture of products useful for the diagnosis and screening for HH. Identification of individuals affected with HH will allow initiation of this therapy, which can prevent symptoms, arrest progression of organ damage, and in some cases reverse pathology due to iron overload.

Moreover, such identification, isolation, and cloning of the gene would enable the study of the operation of the gene in the development of iron overload diseases, in general, and HH in particular. Further, it would be highly desirable to provide therapeutics for iron overload diseases, and HH disease in particular, as well as oxidative free radical diseases, reactions, and processes in general. The identification, isolation, sequencing, and cloning of the gene responsible for the remaining 5–15% of patients indicated with HH who do not possess any mutations of known genes, and identification of its protein products would also facilitate improved therapeutic development.

These and other embodiments of the invention will be apparent from the detailed description and the claims.

SUMMARY OF THE INVENTION

The present inventive subject matter relates to an identified, isolated, cloned and sequenced mutated SLC11A3 gene responsible for HH in about 5–15% of patients indicated with HH who do not possess any mutations of known genes thought to cause HH.

The principal mutation found in the gene comprises a single nucleotide substitution of A-to-C at positions 734 (A734C) in exon 5 which causes a significant amino acid change in the protein product expressed by the gene. One such amino acid change that may cause disruption of normal regulation of SLC11A3 activity as a result is the amino acid substitution of asparagine by histidine at position 144 (N144H).

The present invention, therefore, represents the first opportunity to accurately and noninvasively screen and diagnose HH in the 5–15% of patients indicated with HH who do not possess any mutations of known genes thought to cause HH. In addition, the present invention enables the study of the SLC11A3 gene. Through such study, the development of therapeutics (gene, protein replacement, antibodies, small molecules, and the like) for HH disease will be enabled.

In accordance with a first embodiment of the present invention, there is provided an isolated nucleic acid comprising a nucleic acid sequence corresponding to the nucleic acid sequence of SEQ ID NO: 1.

Another embodiment of the present inventive subject matter is a method for diagnosing a patient as having an increased risk of developing HH disease, comprising the steps of providing DNA or RNA from the individual; and assessing the DNA or RNA for the presence or absence of a base mutation at position 734 (A734C) in exon 5 of the SLC11A3 gene wherein the absence of the base mutation indicates the absence of a HH gene mutation in the genome of the individual and the presence of the base mutation indicates the presence of the HH gene mutation in the genome of the individual and an increase risk of developing HH disease.

Yet another embodiment of the present inventive subject matter is an oligonucleotide in a range of 8–18 consecutive nucleotides selected from a sequence unique to SEQ ID NO: 1 or the complement of SEQ ID NO: 1.

Another embodiment of the present inventive subject matter is a isolated polypeptide comprising the amino acid sequence as shown in SEQ ID NO: 2, SEQ ID NO: 3, or SEQ ID NO: 4, wherein SEQ ID NO: 2, SEQ ID NO: 3, and are the normal peptide product of the SLC11A3 gene, the mutated peptide product of the SLC11A3 gene and the wild type peptide product of the SLC11A3 gene, respectively.

Yet another embodiment of the inventive subject matter is a pharmaceutical composition comprising the isolated polypeptide as shown in SEQ ID NO: 2.

Another embodiment of the present inventive subject matter is a kit for the detection of the presence or absence of a base mutation at position 734 (A734C) of the SLC11A3 gene. In another embodiment, the kit further comprises oligonucleotide primers for amplifying the DNA containing the base-pair polymorphisms.

Yet another embodiment of the present inventive subject matter is a genetic marker predictive of a hereditary hemochromatosis (HH) gene mutation comprising a partial sequence of SEQ ID NO: 1 and sequences complementary therewith. In one aspect, the nucleic acid is DNA. In another aspect, the DNA is cDNA. In another aspect, the nucleic acid is RNA. In another aspect, the nucleic acid is a nucleic acid sequence corresponding to the nucleic acid sequence of SEQ ID NO: 1.

Still yet another embodiment of the present inventive subject matter of the invention is a cloning vector comprising a coding sequence of a nucleic acid as set forth above and a replicon operative in a host cell for the vector.

Further still yet another embodiment of the present inventive subject matter is an expression vector comprising a coding sequence of a nucleic acid set forth above operably linked with a promoter sequence capable of directing expression of the coding sequence in host cells for the vector.

Another embodiment of the present inventive subject matter is host cells transformed with a vector as set forth above.

Yet another embodiment of the present inventive subject matter is a method of producing a mutant SLC11A3 polypeptide comprising: transforming host cells with a vector capable of expressing a polypeptide from a nucleic acid sequence as set forth above; culturing the cells under conditions suitable for production of the polypeptide; and recovering the polypeptide.

Still yet another embodiment of the present inventive subject matter is a peptide product consisting of a polypeptide having the amino acid sequence corresponding to the sequence of SEQ ID NO: 2, SEQ ID NO: 3, or SEQ ID NO: 4. In one aspect, the peptide is labeled. In another aspect, the peptide is a fusion protein.

Further still yet another embodiment of the present inventive subject matter of the invention is a use of a peptide as set forth above as an immunogen for the production of antibodies. In one embodiment, there is provided an antibody produced in such application. In one embodiment, the antibody is labeled. In another embodiment, the antibody is bound to a solid support. In a further embodiment, the antibody is monoclonal. Another embodiment of the present inventive subject matter is an oligonucleotide primer useful for amplification of DNA, the oligonucleotide primer designed on the basis of the DNA sequence of any one of SEQ ID NO: 1.

Yet another embodiment of the present inventive subject matter is a method for diagnosing whether a patient is afflicted with hereditary hemochromatosis (HH) disease, comprising: contacting cells of the patient with antibodies directed against an epitope on an SLC11A3 protein product corresponding substantially to SEQ ID NO: 3, or SEQ ID NO: 4; and observing whether the antibodies localize on the cells. In one embodiment, the method is conducted in vitro. In another embodiment, the method is conducted in vivo.

Still yet another embodiment of the present inventive subject matter is a method for treating a patient diagnosed as having hereditary hemochromatosis (HH) disease, comprising delivering a polypeptide corresponding to the amino acid sequence of SEQ ID NO: 2 to tissues of the patient. In one aspect, the polypeptide is delivered directly to the tissues. In another aspect, the polypeptide is delivered intravenously. In another embodiment, the polypeptide is delivered to the tissues through gene therapy.

Further still yet another embodiment of the present inventive subject matter is an animal model for hereditary hemochromatosis (HH) disease, comprising a mammal possessing a mutant or knocked-out SLC11A3 gene.

Another embodiment of the present inventive subject matter is metal chelation agents derived from nucleic acid sequences described above or from a peptide product as described above in a physiologically acceptable carrier. In one embodiment, the metal is selected from the group consisting of iron, mercury, cadmium, lead, and zinc.

Yet another embodiment of the present inventive subject matter is a method to screen mammals for susceptibility to metal toxicities, comprising, screening such mammals for a mutation in the SLC11A3 gene and wherein those mammals identified as having a mutation are more susceptible to metal toxicities than mammals not identified as having a mutation. In one aspect, the metal is selected from the group consisting of iron, mercury, cadmium, lead, and zinc.

Still yet another embodiment of the present inventive subject matter is a method for selecting patients infected with hepatitis virus for α-interferon treatment, comprising screening such patients for a mutation in the HH gene and wherein those patients not identified as having a mutation are selected to proceed with α-interferon treatment and those identified as having a mutation are selected to undergo phlebotomy prior to α-interferon treatment.

Further still yet another embodiment of the present inventive subject matter is a T-cell differentiation factor comprising a moiety selected from the group consisting of molecules derived from nucleic acid sequences described above and from peptide products described above.

Another embodiment of the present inventive subject matter is a method for screening potential therapeutic agents for activity in connection with HH disease, comprising: providing a screening tool selected from the group consisting of a cell line, a cell free, and a mammal containing or expressing a defective SLC11A3 gene or gene product; contacting the screening tool with the potential therapeutic agent; and assaying the screening tool for an activity selected from the group consisting of SLC11A3 protein folding, iron uptake, iron transport, iron metabolism, receptor-like activities, upstream processes, downstream processes, gene transcription, and signaling events.

Yet another embodiment of the present inventive subject matter is a therapeutic agent for the mitigation of injury due to oxidative processes in vivo, comprising a moiety selected from the group consisting of molecules derived from nucleic acid sequences described above and from peptide products described above.

Yet another embodiment of the present inventive subject matter is a method for diagnosing whether a patient is afflicted with anemia, comprising: contacting cells of the patient with antibodies directed against an epitope on an SLCllA3 protein product corresponding substantially to SEQ ID NO: 3, or SEQ ID NO: 4; and observing whether the antibodies localize on the cells. In one embodiment, the method is conducted in vitro. In another embodiment, the method is conducted in vivo.

Further still yet another embodiment of the present invention involves a kit for detecting or identifying HH or anaemia in a sample, comprising a means for collecting a sample of breast epithelial cells and a means for detecting an A-to-C transversion at position 734 (A734C) in the SLC11A3 gene.

Yet another embodiment of the present invention is directed to a pharmaceutical composition for treating iron overload or anaemia in an animal, comprising a therapeutically effective amount of an catalytically active fragment of an amino acid sequence as shown in SEQ ID NO: 2, SEQ ID NO: 3 or SEQ ID NO: 4, and a pharmaceutically acceptable carrier.

DETAILED DESCRIPTION OF THE INVENTION

As used herein, "marker" refers to a DNA sequence polymorphism flanked by unique regions. These regions flanking the "marker" can be utilized for the design and construction of oligonucleotides for amplifying the relevant DNA portions and detecting the polymorphisms therein.

The term "HH disease" refers to hereditary hemochromatosis disease. The criteria utilized herein to assess whether a patient is affected with the HH disease (i.e., whether the patient is an "affected individual" having "affected chromosomes") has been established by the diagnostic criteria set out in Crawford et al. *Am J Hum Genet* 57:362–367 (1995).

The term "lod score" refers to a statistic that is used to detect genetic linkage and that is equal to the logarithm to base 10 of the ratio of the probability that the data in a linkage experiment would be obtained if the genetic loci under investigation were linked to the probability that the data would be obtained if the loci were not linked.

A. Discovery of the SLC11A3 Gene Mutation

A large Dutch family was used wherein hemochromatosis segregates as a dominant trait among family members. The clinical symptoms in patients from this family were similar to complaints in other HH patients and include joint pains, osteoarthritis,. fatigue, cardiomyopathies. endocrine disorders such as diabetes mellitus. For several markers on chromosome 2q, two point linkage analyses yielded .positive lad score (Table 1).

TABLE 1

| Marker | Recombination fraction (θ) | | | | | | |
|---|---|---|---|---|---|---|---|
| | 0 | .01 | .05 | .10 | .20 | .30 | .40 |
| D2S335 | 0.77 | 1.36 | 1.75 | 1.74 | 1.40 | 0.89 | 0.32 |
| D2S2314 | 1.90 | 1.87 | 1.72 | 1.54 | 1.14 | 0.71 | 0.27 |
| D2S2273 | 0.69 | 1.13 | 1.50 | 1.51 | 1.22 | 0.78 | 0.29 |
| D2S389 | | 2.96 | 2.73 | 2.44 | 1.80 | 1.09 | 0.38 |
| D2S2167 | 0.45 | 0.44 | 0.38 | 0.31 | 0.21 | 0.13 | 0.07 |
| D2S117 | 1.60 | 1.64 | 1.70 | 1.62 | 1.27 | 0.78 | 0.27 |
| D2S311 | 0.99 | 1.04 | 1.14 | 1.13 | 0.91 | 0.55 | 0.16 |
| D2S2392 | 1.59 | 1.55 | 1.41 | 1.23 | 0.86 | 0.48 | 0.17 |
| D2S2289 | 1.06 | 1.11 | 1.18 | 1.15 | 0.91 | 0.57 | 0.22 |
| D2S325 | 0.90 | 0.90 | 0.94 | 0.95 | 0.81 | 0.52 | 0.19 |
| D2S2382 | 1.12 | 1.09 | 1.00 | 0.87 | 0.61 | 0.36 | 0.13 |

Patients were suspected to have HH if they had a blood ferritin level above 450 ng/ml and/or transferrin saturation >50%. This diagnosis was further confirmed by a specialist through liver biopsy and Magnetic Resonance Imaging (MRI). Diseases with similar expression such as Hereditary Hyperferritinemia Cataract Syndrome (HHCS) and aceruloplasnemia were excluded. Patients were treated by putting them on a regular phlebotomy regime.

Genomic DNA was isolated from peripheral blood as described. For the systematic genome scan short tandem repeat polymorphisms (STRPs) from the Genethon markers set were used. Genomic DNA (25 ng) was amplified in 10 ml PCR reactions containing 1× GeneAmp PCR Gold Buffer; 1.5 mM $MgCl_2$; 25 ng of fluorescent forward primer; 25 ng unlabelled reverse primer and 0.4 units of AmpliTag Gold DNA polymerase (Applied Biosystems). Initial denaturation was 15' at 95° C. followed by 32 cycles of 30" denaturation at 95° C., 30" annealing at 55° C. and 90" extension at 72° C. PCR products were pooled and loaded on an ABI377 automated sequencer (filterset D; 5% denaturing FMC LongRanger acrylamide gel), data were analyzed using ABI GeneScan3.1 and ABI Genotyper2.1 software.

Simulation studies using the SLINK program showed that the family was sufficient for finding significant evidence for linkage with an average maximum lod score of Z=3.24 by using the following linkage analysis model: HH was assumed to be a autosomal dominant disorder with a disease gene frequency of 0.001. To account for differences in age at onset of male and female patients three (age and sex dependent) liability classes were defined with penetrances of 0.02, 0.6 and 0.8 for class 1 (male<30, female<40 years), class 2 (male 30–60 and female 40–70 years) and class 3 (male>60, female>70 years), respectively. Two point linkage analysis was performed using the MLINK and ILINK programs of the LINKAGE package (version 5.1). Recombination frequency (q) was assumed to be equal for males and females. Equal allele frequencies were used. For haplotype analyses, phase was assigned on the basis of the minimum number of recombination events.

The highest lod score was obtained with marker D2S389, (Zmax=3.01 at q=0.0). Additional markers were tested from the region and haplotypes constructed therefrom (FIG. 1). Accordingly, it was found that all patients share a common allele for markers D2S389 and D2S2167. However, recombination events were identified for D2S2273 on the centromeric site and D2S117 on the telomeric site. These sites define the critical region to a maximum of 25 cM on the sex average genetic map. This is the fourth locus identified for HH and is named HFE4.

Based on the lod scores, a search for candidate genes in public databases and literature identified a large number of expressed sequence tags and genes with already known function. Of these choices, SLC11A3 was the most likely. SLC11A3 also known as IREG1, MTP1, and FPN1 has been mapped to human chromosome 2q.

B. Characterization and Expression of SLC11A3 Gene

1. Sequence

The human SLC11A3 gene encompasses 20 kb and consists of 8 exons. The open reading frame of 1716 bp starts at position 305 of exon 1 and ends at position 314 of exon 8 encoding a protein of 571 aminoacids with 9 or 10 transmembrarte domains.

Although conflicting evidence exists in the prior art, it has been confirmed that human SLC11A3 is expressed in most tissues but especially in those tissues involved with iron metabolism. Accordingly, expression of SLC11A3 is highest in the digestive tract, liver, placenta, kidneys and monocytes.

SLC11A3 is also a basolateral membrane protein implicated in the movement of iron across the enterocytes into the circulatory system. In particular, SLC11A3 mRNA contains in its 5' untranslated region a stem-loop structure characteristic of an iron responsive element (IRE). This IRE binds to iron responsive proteins 1 and 2 (IRP1 and IRP2) indicating that expression of SLC11A3 is probably regulated by intracellular iron levels.

Moreover, in all symptomatic HH patients, all exons of the mutated SLC11A3 gene including intron-exon boundaries contain a heterozygous A-to-C transversion at position 734 (A734C). Simple statistical analysis compared to 200 healthy controls from the Dutch general population suggests that the heterozygous A-to-C transversion at position 734 (A734C) base change is the causative mutation for HH.

The mutation leads to an amino acid substitution of asparaqine by histidine at position 144 (N144H). Linkage disequilibrium of this mutation with another yet unidentified mutation is possible but this is not likely for a number of reasons. First, no other sequence alteration segregating with the disease was detected. Second, due to the highly conserved nature of asparagirie in vertebrates the substitution of asparagine suggests a pronounced effect on SLC11A3 function.

Several possible results arise from the mutation. Protein structure prediction programs predict that the mutation is expressed in a transmembrane domain which may explain the effect of the mutation on the SLC11A3 structure. Another result may arise from the fact that asparagine is a neutral amino acid, i.e. when asparagine is substituted with the polar histidine the hydrophobicity of the transmembrane domain may induce protein folding. Finally, it is clear that the mutation is important for metal ion binding because it resides within a region of the protein that contains other divalent metal transporters that otherwise show little homology to SLC11A3.

2. Structure/Function of SLC11A3 and Mutated SLC11A3 Gene Product

Ferrous iron (Fe2+) is transported through the apical surface of the enterocytes by the divalent metal transporter (DMT1) wherein a model for iron transport is depicted in FIG. 6. Iron can then be stored as ferritin or transported across the basolateral membrane by SLC11A3 with the aid of hephaestin (Hp). In blood plasma, iron is then loaded onto ferrotransferrin as ferric iron (Fe3+) and subsequently taken up by body tissues such as the liver by transport over a transferrin receptor (TFR2) that is associated with HFE.

Mutated SLC11A3 in HFE4 patients might cause disruption of normal regulation of SLC11A3 activity and lead to transport of excessive amounts of iron out of enterocytes towards the circulation suggesting that the N144H mutation in SLC11A3 is an activating mutation. As a result iron levels in enterocytes are expected to be depleted.

Activity of DMT1 is controlled by intracellular iron levels. Low iron levels will lead to increased iron uptake by DMT1. The excessive uptake of iron from the lumen of the gut and transport of iron to the circulation then leads to accumulation of iron in blood plasma and body tissues. The mutation results in overactivation of SLC11A3.

Thus described, a heterozygous mutation in the SLC11A3 gene is disclosed that explains autosomal dominant hemochromatosis and which may also have important implications for explaining hemochromatosis in the 5–15% of patients who do not carry mutations in the HH and TFR2 genes. Moreover, SLC11A3 is a target for developing therapeutic approaches for anemia as described herein because the activating mutations in SLC11A3 might result indirectly in activation of DMT1 activity.

3. Mutation Analysis

SLC11A3 has been described under several aliases such as iron regulated transporter gene 1(IREG1), metal transport protein 1(MTP1) or solute carrier family 11 member 3 (SLC11A3). (GENBANK accession numbers AF226614, AF231121 and AF215636).

The genomic structure of SLC11A3 was determined by aligning cDNA (AF231121) and genomic (RP11-270G18, AC013439) sequences. SLC11A3 exons (1–8) were amplified from genomic DNA using primers designed to flanking intronic sequence (at least 50 bp intronic sequence on both sides of each exon).

The following primers were used:

```
Exon 1:
Forward primer   5'-3' (F-) CCCCGACTCGGTATAAGAC
                 (SEQ ID NO: 5),
reverse primer   5'-3' (R-) TTCCTCCAGAACTCG TGT AG
                 (SEQ ID NO: 6);

Exon 2:          F-TGGATAAGCATTCTGCCCTC
                 (SEQ ID NO: 7),
                 R-TAAAGCATGTGTACTTGGATG
                 (SEQ ID NO: 8);

Exon 3:          F-AATGTAGCCAGGAAGTGCC
                 (SEQ ID NO: 9),
                 R-AGAGGTGGTGCCATCTAAG
                 (SEQ ID NO: 10);

Exon 4:          F-GGATAAGAACAGTCTCACTG
                 (SEQ ID NO: 11),
                 R-TTCATCCTTTACCACTACCAG
                 (SEQ ID NO: 12);

Exon 5:          F-TTAAA    CTGCCTTGTTTAGTG
                 (SEQ ID NO: 13),
                 R-GCCTCATTTATCACCACCG
                 (SEQ ID NO: 14);

Exon 6:          F-TTGTGTAAATGG    GCAGTCTC
                 (SEQ ID NO: 15),
                 R-CCTCGTCTACCAAAGCGATA
                 (SEQ ID NO: 16);

Exon 7 (part1):  F-GCTTTTATTTCTACAT    GTCC
                 (SEQ ID NO: 17),
                 R-GCTGTGCCAATCCTGAGATC
                 (SEQ ID NO: 18);

Exon 7 (part2):  F-GAGCATCAGCTATAACTG    G
                 (SEQ ID NO: 19),
                 R-TAATGGATTCTCTGAACCTAC
                 (SEQ ID NO: 20);

Exon 8 (part1):  F-TTGAAATGTATGCCTGTAAAC
                 (SEQ ID NO: 21),
                 R-TTTCCATGCCTCAACATAAGG
                 (SEQ ID NO: 22);

Exon 8 (part2):  F-GTTTTTACCACAGCTGTGCC
                 (SEQ ID NO: 23),
                 R-ATACCTTAAGATCAATAGGATC
                 (SEQ ID NO: 24).
```

25 ml PCR reactions contained 2.5 mM dNTP, 1 mM MgCl$_2$, 1.25 unit of Taq polymerase (Gibco BRL) and 25 ng DNA. Amplification was done using 10' initial denaturation at 94° C., 35 cycles of 30" at 94° C., 30" at 55° C. and 1' 72° C. with a final extension of 5' at 72° C. PCR products were purified using the Millipore Multiscreenâ-PCR Plates, and their approximate concentrations estimated using a DNA size standard (BRL) Mutation detection was done by direct sequencing of both strands of PCR products on an ABI377 automated sequencer using BigDye Terminator chemistry (Applied Biosystems). Analysis was done with Factura software and Sequence Navigator (Applied Biosystems) for heterozygous base calls and sequence alignment.

Testing of the base change in exon 5 in remaining family members and controls was done using Allele Specific Oligonucleotide Hybridization (ASO). PCR products containing exon 5 were amplified as described under sequencing. PCR products were blotted onto positively charged membranes. The blots were hybridized at 37° C. for 45' with either the normal (TATTGCAAATTTGGC (SEQ ID NO: 25)) or mutated sequence (TATTGCACATTTGGC (SEQ ID NO: 26)). Filters were washed until a final stringency of 0.3×SSC/0.1% SDS was obtained for 15' at 37° C.

4. Protein Structure Prediction and Amino Acid Alignment

Sequences were found by homology searches of the human protein sequence to the non-redundant database using the BLAST algorithm. Implementing the Clustal-W algorithm the program Vector NTI aligned the sequences.

The protein structure was predicted using PEPTIDE STRUCTURE and PEPPLOT progams from Genetics Computer Groups (GCG) to obtain hydropathy plots. Transmembrane domains were identified and their topography predicted using TopPred, PHDhtm, SOSUI, HMMTOP, TMHMM, Tmpred programs. These programs predicted 9 or 10 transmembrane domains and all predicted the N144H mutation to be in a transmembrane domain.

Northern blots containing multiple adult human tissues (2 mg of polyA mRNA per lane) (Clontech), and multiple adult human digestive system tissues (1 mg of polyA mRNA per lane) (Clontech) and a Northern blot containing human monocytes and lymphoblast cells (10 mg total RNA) were hybridised with a genomic 431 bp. PCR product, from within exon 7 of SLC11A3, using ExpressHybä hybridisation solution (Clontech) according to the manufacturers instructions. Labeling of the probe was done using the Strip-EZ DNAä kit (AMBION).

C. Applications

1. HH Screening

With knowledge of the primary mutation of the mutated SLC11A3 gene as disclosed herein, screening for presymptomatic heterozygotes, including prenatal diagnosis, and screening for heterozygotes can be readily carried out.

There are at least four levels at which the diagnostic information from the mutated SLC11A3 gene can be used. The first is to assist in the medical diagnosis of a symptomatic patient. In this application, a patient with a high index of suspicion for being affected with HH could be tested with the gene-based diagnostic. A positive result would show that the individual was heterozygous for the common HH mutation. This would provide a rapid and non-invasive confirmation that the individual corresponded to the fraction of the population heterozygous for this mutation. Such a result would help rule out other causes of iron overload in that individual.

The second level of application would be in first degree relatives of newly diagnosed probands. Currently recommended medical practice is to screen all such first degree relatives, as they are at a higher risk for disease and, if identified, could benefit from therapeutic intervention.

The third level of screening would be in individuals afflicted with diseases that are known to be sequelae of HH disease. Such diseases include cirrhosis of the liver, diabetes, arthritis, reproductive dysfunction, and heart disease. It has been estimated, for example, that as many as 1% of individuals with diabetes may be so afflicted because of HH disease. In addition, other conditions such as sporadic porphyria cutanea tarda can be screened for using a mutated SLC11A3 gene diagnosis. When secondary to HH disease, some of the pathology of these diseases can be reversed upon phlebotomy therapy. Furthermore, it has been disclosed that the potential for hemochromatosis interferes with the effectiveness of interferon treatment of hepatitis C (Bacon, B. Abstracts of the Fifth Conference of the International Association for the Study of Disorders of Iron Metabolism 15–16 1995)). Therefore, it will be beneficial to perform screening with gene-based diagnostics in these disease populations.

The fourth level of screening is to screen the general population for heterozygotes. Several cost-benefit analyses have suggested that there is value in such screenings for the identification of presymptomatic individuals. Once identified, such individuals could be targeted for preventative phlebotomy or treatment with the therapeutic compositions of the invention.

2. Nucleic Acid Based Screening

Individuals carrying mutations in the SLC11A3 gene may be detected at either the DNA, the RNA, or the protein level using a variety of techniques that are well known in the art. The genomic DNA used for the diagnosis may be obtained from body cells, such as those present in peripheral blood, urine, saliva, bucca, surgical specimen, and autopsy specimens. The DNA may be used directly or may be amplified enzymatically in vitro through use of PCR (Saiki et al. Science 239:487–491 (1988)) or other in vitro amplification methods such as the ligase chain reaction (LCR) (Wu and Wallace Genomics 4:560–569 (1989)), strand displacement amplification (SDA) (Walker et al. Proc. Natl. Acad. Sci. U.S.A. 89:392–396 (1992)), self-sustained sequence replication (3SR) (Fahy et al. PCR Methods Appl. 1:25–33 (1992)), prior to mutation analysis. The methodology for preparing nucleic acids in a form that is suitable for mutation detection is well known in the art.

The detection of mutations in specific DNA sequences, such as in the SLC11A3 gene, can be accomplished by a variety of methods including, but not limited to, restriction-fragment-length-polymorphism detection based on allele-specific restriction-endonuclease cleavage (Kan and Dozy Lancet ii:910–912 (1978)), hybridization with allele-specific oligonucleotide probes (Wallace et al. Nucl Acids Res 6:3543–3557 (1978)), including immobilized oligonucleotides (Saiki et al. Proc. Natl. Acad. Sci. U.S.A. 86:6230–6234 (1989)) or oligonucleotide arrays (Maskos and Southern Nucl Acids Res 21:2269–2270 (1993)), allele-specific PCR (Newton et al. Nucl Acids Res 17:2503–2516 (1989)), mismatch-repair detection (MRD) (Faham and Cox Genome Res 5:474–482 (1995)), binding of MutS protein (Wagner et al. Nucl Acids Res 23:3944–3948 (1995), denaturing-gradient gel electrophoresis (DGGE) (Fisher and Lerman et al. Proc. Natl. Acad. Sci. U.S.A. 80:1579–1583 (1983)), single-strand-conformation-polymorphism detection (Orita et al. Genomics 5:874–879 (1983)), RNAase cleavage at mismatched base-pairs (Myers et al. Science 230:1242 (1985)), chemical (Cotton et al. Proc. Natl. Acad. Sci. U.S.A. 85:4397–4401 (1988)) or enzymatic (Youil et al. Proc. Natl. Acad. Sci. U.S.A. 92:87–91 (1995)) cleavage of heteroduplex DNA, methods based on allele specific primer extension (Syvanen et al. Genomics 8:684–692 (1990)), genetic bit analysis (GBA) (Nikiforov et al. Nucl Acids Res 22:4167–4175 (1994)), the oligonucleotide-ligation assay (OLA) (Landegren et al. Science 241:1077 (1988)), the allele-specific ligation chain reaction (LCR) (Barrany Proc. Natl. Acad. Sci. U.S.A. 88:189–193 (1991)), gap-LCR (Abravaya et al. Nucl Acids Res 23:675–682 (1995)), and radioactive and/or fluorescent DNA sequencing using standard procedures well known in the art.

In addition to the genotype described above, single base-pair polymorphisms can also be used to assist in the identification of an individual whose genome contains the SLC11A3 mutation using procedures well known in the art.

3. Antibodies

As mentioned above, antibodies can also be used for the screening of the presence of the mutant SLC11A3, and the protein products therefrom. In addition, antibodies are useful in a variety of other contexts in accordance with the present invention. As will be appreciated, antibodies can be raised against various epitopes of the mutant SLC11A3 protein. Such antibodies can be utilized for the diagnosis of HH and, in certain applications, targeting of affected tissues.

Thus, in accordance with another aspect of the present invention a kit is provided that is suitable for use in screening and assaying for the presence of the mutated SLC11A3 gene by an immunoassay through use of an antibody which specifically binds to a gene product of the mutated SLC11A3 gene in combination with a reagent for detecting the binding of the antibody to the gene product.

Antibodies raised in accordance with the invention can also be utilized to provide extensive information on the characteristics of the protein and of the disease process and other valuable information by process well known in the art.

4. Peptide Presentation Assay

Peptide presentation can be measured through use of a number of well known techniques. One method is to express the SLC11A3 gene product on the surface of mammalian cells. Thereafter, the SLC11A3 gene product can be purified from the cell surface analyzed for peptide binding, through, for example, high performance liquid chromatography (HPLC) after elution. Amino acid sequences of any bound peptides can be determined through conventional sequencing techniques.

Another technique to analyze peptide presentation is to express the SLC11A3 mutated gene product on a cell that does not conventionally possess peptide presentation activity. In such a system, MHC Class I molecules are expressed on the cell surface "empty" (i.e., without any bound peptide). Thereafter, through the addition of a particular peptide to the system, the binding of the particular peptide to the empty Class I molecule can be measured. A similar assay can be utilized in connection with the SLC11A3 mutated gene products.

The present inventive subject matter also contemplates kits for use in determining iron overload or iron underload potential, specifically kits identifying HH or anaemia in a patient. Preferred kit components generally are those that detect the agents discussed herein.

The kits may include one or more control results, such as reference slides of cyto-chemical results characteristic of high and low iron overload or underload potential, or reference slides of in situ hybridization results characteristic in the same regard. Preferably kits will include a control series for interpreting results. The control series may be in the form of one or more photographs or may be depicted in other ways, including written descriptions.

A preferred kit contemplates treating HH, comprising a catalytically active fragment of an amino acid sequence as shown in SEQ ID NO: 2, SEQ ID NO: 3 or SEQ ID NO: 4 in a pharmaceutically acceptable carrier and a device for delivery of the catalytically active fragment to the cells in need thereof, wherein the catalytically active fragment, the carrier and the device are packaged in a container.

Another preferred embodiment is a kit for detecting or identifying HH or anaemia, comprising: a) means for collecting a sample of DNA; and b) means for detecting a catalytically active fragment of an DNA sequence as shown in SEQ ID NO: 1, in the DNA sample.

5. Therapeutics

Identification of the SLC11A3 mutated gene and its gene product also has therapeutic implications. Envisioned are pharmacological, protein replacement, antibody therapy, and gene therapy approaches. In addition, the development of animal models useful for developing therapies and for understanding the molecular mechanisms of HH disease are envisioned. Under a pharmaceutical approach, drugs which circumvent or overcome the mutated SLC11A3 gene function may be designed. Accordingly, agents or drugs which are designed to interact with different aspects of the SLC11A3 protein structure or function or which mimic the SLC11A3 protein interaction with other molecules can modulate SLC11A3 gene function.

Alternatively, a drug might bind to a specific functional residue(s) thereby, increasing or decreasing the affinity for ligand, substrate or cofactor. The assay for such a compound would be to promote or inhibit an interaction between the HH protein and similar molecules.

The present invention also relates to the use of polypeptide or protein replacement therapy for those individuals determined to have a mutated SLC11A3 gene. Treatment of HH disease could be performed by replacing the mutated SLC11A3 protein with normal protein or its functional equivalent in therapeutic amounts.

The present invention also relates to a pharmaceutical composition comprising: (i) a catalytically active fragment of an amino acid sequence as shown in SEQ ID NO: 2, SEQ ID NO: 3 or SEQ ID NO: 4 and (ii) a pharmaceutically acceptable carrier.

The above discussion relating to the utility and administration of the compounds of the present invention also applies to the pharmaceutical compositions of the present invention.

The term "pharmaceutically acceptable carrier" as used herein refers to any carrier, diluent, excipient, suspending agent, lubricating agent, adjuvant, vehicle, delivery system, emulsifier, disintegrant, absorbant, preservative, surfactant, colorant, flavorant, or sweetener.

For these purposes the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

For oral administration, the compounds of the present invention may be provided in any suitable dosage form known in the art. For example, the compositions may be incorporated into tablets, powders, granules, beads, chewable lozenges, capsules, liquids, aqueous suspensions or solutions, or similar dosage forms, using conventional equipment and techniques known in the art. Tablet dosage forms are preferred. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient.

When preparing dosage form incorporating the compositions of the invention, the compounds may also be blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethylcellulose and sodium starch glycolate; suspending agents, such as povidone, polyvinyl alcohol, and the like; absorbents, such as silicon dioxide; preservatives, such as methylparaben, propylparaben, and sodium benzoate; surfactants, such as sodium lauryl sulfate, polysorbate 80, and the like; colorants such as F.D.& C. dyes and lakes; flavorants; and sweeteners.

Compositions and methods of the invention also may utilize controlled release technology. Thus, for example, the inventive compounds may be incorporated into a hydrophobic polymer matrix for controlled release over a period of days. Such controlled release films are well known to the art. Particularly preferred are transdermal delivery systems. Other examples of polymers commonly employed for this purpose that may be used in the present invention include nondegradable ethylene-vinyl acetate copolymer and degradable lactic acid-glycolic acid copolymers which may be used externally or internally. Certain hydrogels such as poly(hydroxyethylmethacrylate) or poly(vinylalcohol) also may be useful, but for shorter release cycles then the other polymer releases systems, such as those mentioned above.

To be effective therapeutically as central nervous system targets, the compounds of the present invention should readily penetrate the blood-brain barrier when peripherally administered. Compounds which cannot penetrate the blood-brain barrier can be effectively administered by an intraventricular route or other appropriate delivery system suitable for administration to the brain.

The compounds of the present invention may be administered in the form of sterile injectable preparations, for example, as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil may be employed including synthetic mono- or di-glycerides. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

The compounds of this invention may also be administered rectally in the form of suppositories. These compositions can be prepared by mixing the drug with a suitable non-irritating excipient which is solid at room temperature, but liquid at rectal temperature and, therefore, will melt in the rectum to release the drug.

Such materials include cocoa butter, beeswax and polyethylene glycols.

The compounds of this invention may also be administered topically, especially when the conditions addressed for treatment involve areas or organs readily accessible by topical application, including neurological disorders of the eye, the skin, or the lower intestinal tract. Suitable topical formulations are readily prepared for each of these areas.

For topical application to the eye, or ophthalmic use, the compounds can be formulated as micronized suspensions in isotonic, pH adjusted sterile saline, or, preferably, as solutions in isotonic, pH adjusted sterile saline, either with or without a preservative such as benzylalkonium chloride. Alternatively for the ophthalmic uses the compounds may be formulated in an ointment such as petrolatum.

For topical application to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract an be effected in a rectal suppository formulation (see above) or in a suitable enema formulation.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

The compounds as referenced above can be administered with other drugs treating HH or anaemia. The dosage level of other drugs will depend upon factors and the effectiveness of the drug combination known to those skilled in the art.

Gene therapy utilizing recombinant DNA technology in vivo is also contemplated within the scope of the present invention. It is within the scope of the invention to deliver the normal form of the SLC11A3 gene into patient cells or vectors which will supply the patient with gene product. In gene therapy of HH disease, a normal version of the SLC11A3 gene is delivered to affected tissue(s) in a form and amount such that the correct gene is expressed and will prepare sufficient quantities of SLC11A3 protein to reverse the effects of the mutated SLC11A3 gene. Current approaches to gene therapy include viral vectors, cell-based delivery systems and delivery agents.

Further, ex vivo gene therapy could also be useful. In ex vivo gene therapy, cells (either autologous or otherwise) are transfected with the normal SLC11A3 gene or a portion thereof and implanted or otherwise delivered into the patient. Such cells thereafter express the normal SLC11A3 gene product in vivo and would be expected to assist a patient with HH disease in avoiding iron overload normally associated with HH disease. Ex vivo gene therapy is described in U.S. Pat. No. 5,399,346 to Anderson et al., the disclosure of which is hereby incorporated by reference in its entirety. Conversely, ex vivo gene therapy in patients suffering from anemia would be expected to assist a patient by promoting iron uptake by introducing cells transfected with mutated SLC11A3.

The invention being thus described, it will be obvious that the same may be varied in many ways. Such variations are not to be regarded as a departure from the spirit scope of the invention and all such modifications are intended to be included within the scope of the following claims.

We claim:

1. An isolated DNA sequence comprising SEQ ID NO: 1 or the complement.

2. The isolated DNA sequence of claim 1, wherein said DNA sequence is cDNA.

3. A method for determining whether an individual has an increased risk of developing HH disease comprising:
   obtaining SLC11A3 DNA from the individual and
   assessing the SLC11A3 DNA sequence for the identity of the nucleotide at position 734 (A734C) of SEQ ID NO: 1,
   wherein the presence of the A nucleotide indicates the absence of a HH gene mutation in the genome of the individual and
   wherein the presence of the C nucleotide indicates the presence of the HH gene mutation and an increased risk of developing HH disease in the genome of the individual.

4. The method of claim 3, wherein the assessing step is performed by a process which comprises subjecting the isolated DNA sequence to amplification using oligonucleotide primers flanking the base-pair mutation.

5. The method of claim 4, wherein the assessing step further comprises an oligonucleotide ligation assay.

6. A kit for diagnosing an individual as having an increased risk of developing HH disease, comprising:
   an isolated DNA sequence of SEQ ID NO: 1 or the complement.

* * * * *

SEQUENCE LISTING

```
<160> NUMBER OF SEQ ID NOS: 26

<210> SEQ ID NO 1
<211> LENGTH: 2443
<212> TYPE: DNA
<213> ORGANISM: Homo sapiens
<220> FEATURE:
<221> NAME/KEY: mutation
<222> LOCATION: (733)..(735)

<400> SEQUENCE: 1
agctggctca gggcgtccgc taggctcgga cgacctgctg agcctcccaa accgcttcca        60
taaggctttg ctttccaact tcagctacag tgttagctaa gtttggaaag aaggaaaaaa       120
gaaaatccct gggcccctttt tcttttgttc tttgccaaag tcgtcgttgt agtcttttg       180 cccaaggctg ttgtgttttt agaggtgcta tctccagttc cttgcactcc tgttaacaag       240
```

-continued

```
cacctcagcg agagcagcag cagcgatagc agccgcagaa gagccagcgg ggtcgcctag    300
tgtcatgacc agggcgggag atcacaaccg ccagagagga tgctgtggat ccttggccga    360
ctacctgacc tctgcaaaat tccttctcta ccttggtcat tctctctcta cttggggaga    420
tcggatgtgg cactttgcgg tgtctgtgtt tctggtagag ctctatggaa acagcctcct    480
tttgacagca gtctacgggc tggtggtggc agggtctgtt ctggtcctgg gagccatcat    540
cggtgactgg gtggacaaga atgctagact aaaagtggcc cagacctcgc tggtggtaca    600
gaatgtttca gtcatcctgt gtggaatcat cctgatgatg gttttcttac ataaacatga    660
rcttctgacc atgtaccatg gatgggttct cacttcctgc tatatcctga tcatcactat    720
tgcaaatatt gcacatttgg ccagtactgc tactgcaatc acaatccaaa gggattggat    780
tgttgttgtt gcaggagaag acagaagcaa actagcaaat atgaatgcca caatacgaag    840
gattgaccag ttaaccaaca tcttagcccc catggctgtt ggccagatta tgacatttgg    900
ctccccagtc atcggctgtg ctttatttc gggatggaac ttggtatcca tgtgcgtgga    960
gtacgtcctg ctctggaagg tttaccagaa acccagct ctagctgtga agctggtct     1020 taaagaagag gaaactgaat tgaaacagct gaatttacac aaagatactg agccaaaacc    1080
cctggaggga actcatctaa tgggtgtgaa ggactctaac atccatgagc ttgaacatga    1140
gcaagagcct acttgtgcct cccagatggc tgagcccttc cgtaccttcc gagatggatg    1200
ggtctcctac tacaaccagc ctgtgtttct ggctggcatg ggtcttgctt tcctttatat    1260
gactgtcctg ggctttgact gcatcaccac agggtacgcc tacactcagg gactgagtgg    1320
ttccatcctc agtatttga tgggagcatc agctataact ggaataatgg gaactgtagc    1380
ttttacttgg ctacgtcgaa aatgtggttt ggttcggaca ggtctgatct caggattggc    1440
acagctttcc tgtttgatct tgtgtgtgat ctctgtattc atgcctggaa gcccctgga    1500 cttgtccgtt tctccttttg aagatatccg atcaaggttc attcaaggag agtcaattac    1560
acctaccaag atacctgaaa ttacaactga atatacatg tctaatgggt ctaattctgc     1620
taatattgtc ccggagacaa gtcctgaatc tgtgcccata atctctgtca gtctgctgtt    1680
tgcaggcgtc attgctgcta gaatcggtct ttggtccttt gatttaactg tgacacagtt    1740
gctgcaagaa aatgtaattg aatctgaaag aggcattata aatggtgtac agaactccat    1800
gaactatctt cttgatcttc tgcatttcat catggtcatc ctggctccaa atcctgaagc    1860
ttttggcttg ctcgtattga tttcagtctc ctttgtggca atgggccaca ttatgtattt    1920
ccgatttgcc caaaatactc tgggaaacaa gctctttgct tgcggtcctg atgcaaaaga    1980
agttaggaag gaaaatcaag caaatacatc tgttgtttga gacagtttaa ctgttgctat    2040
cctgttacta gattatatag agcacatgtg cttatttgt actgcagaat tccaataaat    2100
ggctgggtgt tttgctctgt ttttaccaca gctgtgcctt gagaactaaa agctgtttag    2160
gaaacctaag tcagcagaaa ttaactgatt aatttccctt atgttgaggc atggraaaaa    2220
aattggraaa aggaaaaact cagttttaaa tacgggagac tataatggat aacactgrat    2280
tcccctattt ctcatgagta gatacaatct tacgtaaaag agtggttagt cacgtgaatt    2340
cagttatcat ttgacagatt cttatctgta ctagaattca gatatgtcag ttttctgcaa    2400
aactcactct tgttcaagac tagctaattt attttttttgc atc                    2443
```

<210> SEQ ID NO 2
<211> LENGTH: 571
<212> TYPE: PRT

<213> ORGANISM: Homo sapiens

<400> SEQUENCE: 2

```
Met Thr Arg Ala Gly Asp His Asn Arg Gln Arg Gly Cys Cys Gly Ser
1               5                   10                  15

Leu Ala Asp Tyr Leu Thr Ser Ala Lys Phe Leu Leu Tyr Leu Gly His
            20                  25                  30

Ser Leu Ser Thr Trp Gly Asp Arg Met Trp His Phe Ala Val Ser Val
        35                  40                  45

Phe Leu Val Glu Leu Tyr Gly Asn Ser Leu Leu Leu Thr Ala Val Tyr
    50                  55                  60

Gly Leu Val Val Ala Gly Ser Val Leu Val Leu Gly Ala Ile Ile Gly
65                  70                  75                  80

Asp Trp Val Asp Lys Asn Ala Arg Leu Lys Val Ala Gln Thr Ser Leu
                85                  90                  95

Val Val Gln Asn Val Ser Val Ile Leu Cys Gly Ile Ile Leu Met Met
            100                 105                 110

Val Phe Leu His Lys His Glu Leu Leu Thr Met Tyr His Gly Trp Val
        115                 120                 125

Leu Thr Ser Cys Tyr Ile Leu Ile Ile Thr Ile Ala Asn Ile Ala Asp
    130                 135                 140

Leu Ala Ser Thr Ala Thr Ala Ile Thr Ile Gln Arg Asp Trp Ile Val
145                 150                 155                 160

Val Val Ala Gly Glu Asp Arg Ser Lys Leu Ala Asn Met Asn Ala Thr
                165                 170                 175

Ile Arg Arg Ile Asp Gln Leu Thr Asn Ile Leu Ala Pro Met Ala Val
            180                 185                 190

Gly Gln Ile Met Thr Phe Gly Ser Pro Val Ile Gly Cys Gly Phe Ile
        195                 200                 205

Ser Gly Trp Asn Leu Val Ser Met Cys Val Glu Tyr Val Leu Leu Trp
    210                 215                 220

Lys Val Tyr Gln Lys Thr Pro Ala Leu Ala Val Lys Ala Gly Leu Lys
225                 230                 235                 240

Glu Glu Glu Thr Glu Leu Lys Gln Leu Asn Leu His Lys Asp Thr Glu
                245                 250                 255

Pro Lys Pro Leu Glu Gly Thr His Leu Met Gly Val Lys Asp Ser Asn
            260                 265                 270

Ile His Glu Leu Glu His Glu Gln Glu Pro Thr Cys Ala Ser Gln Met
        275                 280                 285

Ala Glu Pro Phe Arg Thr Phe Arg Asp Gly Trp Val Ser Tyr Tyr Asn
    290                 295                 300

Gln Pro Val Phe Leu Ala Gly Met Gly Leu Ala Phe Leu Tyr Met Thr
305                 310                 315                 320

Val Leu Gly Phe Asp Cys Ile Thr Thr Gly Tyr Ala Tyr Thr Gln Gly
                325                 330                 335

Leu Ser Gly Ser Ile Leu Ser Ile Leu Met Gly Ala Ser Ala Ile Thr
            340                 345                 350

Gly Ile Met Gly Thr Val Ala Phe Thr Trp Leu Arg Arg Lys Cys Gly
        355                 360                 365

Leu Val Arg Thr Gly Leu Ile Ser Gly Leu Ala Gln Leu Ser Cys Leu
    370                 375                 380

Ile Leu Cys Val Ile Ser Val Phe Met Pro Gly Ser Pro Leu Asp Leu
385                 390                 395                 400
```

-continued

```
Ser Val Ser Pro Phe Glu Asp Ile Arg Ser Arg Phe Ile Gln Gly Glu
                405                 410                 415

Ser Ile Thr Pro Thr Lys Ile Pro Glu Ile Thr Thr Glu Ile Tyr Met
                420                 425                 430

Ser Asn Gly Ser Asn Ser Ala Asn Ile Val Pro Glu Thr Ser Pro Glu
                435                 440                 445

Ser Val Pro Ile Ile Ser Val Ser Leu Leu Phe Ala Gly Val Ile Ala
                450                 455                 460

Ala Arg Ile Gly Leu Trp Ser Phe Asp Leu Thr Val Thr Gln Leu Leu
465                 470                 475                 480

Gln Gln Asn Val Ile Glu Ser Glu Arg Gly Ile Ile Asn Gly Val Gln
                485                 490                 495

Asn Ser Met Asn Tyr Leu Leu Asp Leu Leu His Phe Ile Met Val Ile
                500                 505                 510

Leu Ala Pro Asn Pro Glu Ala Phe Gly Leu Leu Val Leu Ile Ser Val
                515                 520                 525

Ser Phe Val Ala Met Gly His Ile Met Tyr Phe Arg Phe Ala Gln Asn
                530                 535                 540

Thr Leu Gly Asn Lys Leu Phe Ala Cys Gly Pro Asp Ala Lys Glu Val
545                 550                 555                 560

Arg Lys Glu Asn Gln Ala Asn Thr Ser Val Val
                565                 570

<210> SEQ ID NO 3
<211> LENGTH: 571
<212> TYPE: PRT
<213> ORGANISM: Homo sapiens
<220> FEATURE:
<221> NAME/KEY: VARIANT
<222> LOCATION: (144)..(144)

<400> SEQUENCE: 3

Met Thr Arg Ala Gly Asp His Asn Arg Gln Arg Gly Cys Cys Gly Ser
1               5                   10                  15

Leu Ala Asp Tyr Leu Thr Ser Ala Lys Phe Leu Leu Tyr Leu Gly His
                20                  25                  30

Ser Leu Ser Thr Trp Gly Asp Arg Met Trp His Phe Ala Val Ser Val
                35                  40                  45

Phe Leu Val Glu Leu Tyr Gly Asn Ser Leu Leu Leu Thr Ala Val Tyr
                50                  55                  60

Gly Leu Val Val Ala Gly Ser Val Leu Val Leu Gly Ala Ile Ile Gly
65                  70                  75                  80

Asp Trp Val Asp Lys Asn Ala Arg Leu Lys Val Ala Gln Thr Ser Leu
                85                  90                  95

Val Val Gln Asn Val Ser Val Ile Leu Cys Gly Ile Ile Leu Met Met
                100                 105                 110

Val Phe Leu His Lys His Glu Leu Leu Thr Met Tyr His Gly Trp Val
                115                 120                 125

Leu Thr Ser Cys Tyr Ile Leu Ile Ile Thr Ile Ala Asn Ile Ala His
                130                 135                 140

Leu Ala Ser Thr Ala Thr Ala Ile Thr Ile Gln Arg Asp Trp Ile Val
145                 150                 155                 160

Val Val Ala Gly Glu Asp Arg Ser Lys Leu Ala Asn Met Asn Ala Thr
                165                 170                 175

Ile Arg Arg Ile Asp Gln Leu Thr Asn Ile Leu Ala Pro Met Ala Val
                180                 185                 190
```

```
Gly Gln Ile Met Thr Phe Gly Ser Pro Val Ile Gly Cys Gly Phe Ile
            195                 200                 205
Ser Gly Trp Asn Leu Val Ser Met Cys Val Glu Tyr Val Leu Leu Trp
        210                 215                 220
Lys Val Tyr Gln Lys Thr Pro Ala Leu Ala Val Lys Ala Gly Leu Lys
225                 230                 235                 240
Glu Glu Glu Thr Glu Leu Lys Gln Leu Asn Leu His Lys Asp Thr Glu
                245                 250                 255
Pro Lys Pro Leu Glu Gly Thr His Leu Met Gly Val Lys Asp Ser Asn
            260                 265                 270
Ile His Glu Leu Glu His Glu Gln Glu Pro Thr Cys Ala Ser Gln Met
        275                 280                 285
Ala Glu Pro Phe Arg Thr Phe Arg Asp Gly Trp Val Ser Tyr Tyr Asn
        290                 295                 300
Gln Pro Val Phe Leu Ala Gly Met Gly Leu Ala Phe Leu Tyr Met Thr
305                 310                 315                 320
Val Leu Gly Phe Asp Cys Ile Thr Thr Gly Tyr Ala Tyr Thr Gln Gly
                325                 330                 335
Leu Ser Gly Ser Ile Leu Ser Ile Leu Met Gly Ala Ser Ala Ile Thr
            340                 345                 350
Gly Ile Met Gly Thr Val Ala Phe Thr Trp Leu Arg Arg Lys Cys Gly
        355                 360                 365
Leu Val Arg Thr Gly Leu Ile Ser Gly Leu Ala Gln Leu Ser Cys Leu
        370                 375                 380
Ile Leu Cys Val Ile Ser Val Phe Met Pro Gly Ser Pro Leu Asp Leu
385                 390                 395                 400
Ser Val Ser Pro Phe Glu Asp Ile Arg Ser Arg Phe Ile Gln Gly Glu
                405                 410                 415
Ser Ile Thr Pro Thr Lys Ile Pro Glu Ile Thr Thr Glu Ile Tyr Met
            420                 425                 430
Ser Asn Gly Ser Asn Ser Ala Asn Ile Val Pro Glu Thr Ser Pro Glu
        435                 440                 445
Ser Val Pro Ile Ile Ser Val Ser Leu Leu Phe Ala Gly Val Ile Ala
        450                 455                 460
Ala Arg Ile Gly Leu Trp Ser Phe Asp Leu Thr Val Thr Gln Leu Leu
465                 470                 475                 480
Gln Glu Asn Val Ile Glu Ser Glu Arg Gly Ile Ile Asn Gly Val Gln
                485                 490                 495
Asn Ser Met Asn Tyr Leu Leu Asp Leu Leu His Phe Ile Met Val Ile
            500                 505                 510
Leu Ala Pro Asn Pro Glu Ala Phe Gly Leu Leu Val Leu Ile Ser Val
        515                 520                 525
Ser Phe Val Ala Met Gly His Ile Met Tyr Phe Arg Phe Ala Gln Asn
        530                 535                 540
Thr Leu Gly Asn Lys Leu Phe Ala Cys Gly Pro Asp Ala Lys Glu Val
545                 550                 555                 560
Arg Lys Glu Asn Gln Ala Asn Thr Ser Val Val
                565                 570

<210> SEQ ID NO 4
<211> LENGTH: 571
<212> TYPE: PRT
<213> ORGANISM: Homo sapiens
<220> FEATURE:
```

```
<221> NAME/KEY: MISC_FEATURE
<222> LOCATION: (144)..(144)
<223> OTHER INFORMATION: Xaa = any amino acid except Asp

<400> SEQUENCE: 4
```

| | | | | | | | | | | | | | | | |
|---|---|---|---|---|---|---|---|---|---|---|---|---|---|---|---|
| Met | Thr | Arg | Ala | Gly | Asp | His | Asn | Arg | Gln | Arg | Gly | Cys | Cys | Gly | Ser |
| 1 | | | | 5 | | | | | 10 | | | | | 15 | |
| Leu | Ala | Asp | Tyr | Leu | Thr | Ser | Ala | Lys | Phe | Leu | Leu | Tyr | Leu | Gly | His |
| | | | 20 | | | | | 25 | | | | | 30 | | |
| Ser | Leu | Ser | Thr | Trp | Gly | Asp | Arg | Met | Trp | His | Phe | Ala | Val | Ser | Val |
| | | | 35 | | | | 40 | | | | | 45 | | | |
| Phe | Leu | Val | Glu | Leu | Tyr | Gly | Asn | Ser | Leu | Leu | Thr | Ala | Val | Tyr | |
| | 50 | | | | | 55 | | | | | 60 | | | | |
| Gly | Leu | Val | Val | Ala | Gly | Ser | Val | Leu | Val | Leu | Gly | Ala | Ile | Ile | Gly |
| 65 | | | | | 70 | | | | | 75 | | | | | 80 |
| Asp | Trp | Val | Asp | Lys | Asn | Ala | Arg | Leu | Lys | Val | Ala | Gln | Thr | Ser | Leu |
| | | | | 85 | | | | | 90 | | | | | 95 | |
| Val | Val | Gln | Asn | Val | Ser | Val | Ile | Leu | Cys | Gly | Ile | Ile | Leu | Met | Met |
| | | | | 100 | | | | | 105 | | | | | 110 | |
| Val | Phe | Leu | His | Lys | His | Glu | Leu | Leu | Thr | Met | Tyr | His | Gly | Trp | Val |
| | | | | 115 | | | | | 120 | | | | | 125 | |
| Leu | Thr | Ser | Cys | Tyr | Ile | Leu | Ile | Ile | Thr | Ile | Ala | Asn | Ile | Ala | Xaa |
| | | 130 | | | | | 135 | | | | | 140 | | | |
| Leu | Ala | Ser | Thr | Ala | Thr | Ala | Ile | Thr | Ile | Gln | Arg | Asp | Trp | Ile | Val |
| 145 | | | | | 150 | | | | | 155 | | | | | 160 |
| Val | Val | Ala | Gly | Glu | Asp | Arg | Ser | Lys | Leu | Ala | Asn | Met | Asn | Ala | Thr |
| | | | | 165 | | | | | 170 | | | | | 175 | |
| Ile | Arg | Arg | Ile | Asp | Gln | Leu | Thr | Asn | Ile | Leu | Ala | Pro | Met | Ala | Val |
| | | | 180 | | | | | 185 | | | | | 190 | | |
| Gly | Gln | Ile | Met | Thr | Phe | Gly | Ser | Pro | Val | Ile | Gly | Cys | Gly | Phe | Ile |
| | | | 195 | | | | | 200 | | | | | 205 | | |
| Ser | Gly | Trp | Asn | Leu | Val | Ser | Met | Cys | Val | Glu | Tyr | Val | Leu | Leu | Trp |
| | 210 | | | | | 215 | | | | | 220 | | | | |
| Lys | Val | Tyr | Gln | Lys | Thr | Pro | Ala | Leu | Ala | Val | Lys | Ala | Gly | Leu | Lys |
| 225 | | | | | 230 | | | | | 235 | | | | | 240 |
| Glu | Glu | Glu | Thr | Glu | Leu | Lys | Gln | Leu | Asn | Leu | His | Lys | Asp | Thr | Glu |
| | | | | 245 | | | | | 250 | | | | | 255 | |
| Pro | Lys | Pro | Leu | Glu | Gly | Thr | His | Leu | Met | Gly | Val | Lys | Asp | Ser | Asn |
| | | | 260 | | | | | 265 | | | | | 270 | | |
| Ile | His | Glu | Leu | Glu | His | Glu | Gln | Glu | Pro | Thr | Cys | Ala | Ser | Gln | Met |
| | | 275 | | | | | 280 | | | | | 285 | | | |
| Ala | Glu | Pro | Phe | Arg | Thr | Phe | Arg | Asp | Gly | Trp | Val | Ser | Tyr | Tyr | Asn |
| | 290 | | | | | 295 | | | | | 300 | | | | |
| Gln | Pro | Val | Phe | Leu | Ala | Gly | Met | Gly | Leu | Ala | Phe | Leu | Tyr | Met | Thr |
| 305 | | | | | 310 | | | | | 315 | | | | | 320 |
| Val | Leu | Gly | Phe | Asp | Cys | Ile | Thr | Thr | Gly | Tyr | Ala | Tyr | Thr | Gln | Gly |
| | | | | 325 | | | | | 330 | | | | | 335 | |
| Leu | Ser | Gly | Ser | Ile | Leu | Ser | Ile | Leu | Met | Gly | Ala | Ser | Ala | Ile | Thr |
| | | | 340 | | | | | 345 | | | | | 350 | | |
| Gly | Ile | Met | Gly | Thr | Val | Ala | Phe | Thr | Trp | Leu | Arg | Arg | Lys | Cys | Gly |
| | | | 355 | | | | | 360 | | | | | 365 | | |
| Leu | Val | Arg | Thr | Gly | Leu | Ile | Ser | Gly | Leu | Ala | Gln | Leu | Ser | Cys | Leu |
| | 370 | | | | | 375 | | | | | 380 | | | | |
| Ile | Leu | Cys | Val | Ile | Ser | Val | Phe | Met | Pro | Gly | Ser | Pro | Leu | Asp | Leu |

-continued

```
            385                 390                 395                 400
    Ser Val Ser Pro Phe Glu Asp Ile Arg Ser Arg Phe Ile Gln Gly Glu
                    405                 410                 415
    Ser Ile Thr Pro Thr Lys Ile Pro Glu Ile Thr Thr Glu Ile Tyr Met
                    420                 425                 430
    Ser Asn Gly Ser Asn Ser Ala Asn Ile Val Pro Glu Thr Ser Pro Glu
                    435                 440                 445
    Ser Val Pro Ile Ile Ser Val Ser Leu Leu Phe Ala Gly Val Ile Ala
                    450                 455                 460
    Ala Arg Ile Gly Leu Trp Ser Phe Asp Leu Thr Val Thr Gln Leu Leu
    465                 470                 475                 480
    Gln Glu Asn Val Ile Glu Ser Glu Arg Gly Ile Ile Asn Gly Val Gln
                    485                 490                 495
    Asn Ser Met Asn Tyr Leu Leu Asp Leu Leu His Phe Ile Met Val Ile
                    500                 505                 510
    Leu Ala Pro Asn Pro Glu Ala Phe Gly Leu Leu Val Leu Ile Ser Val
                    515                 520                 525
    Ser Phe Val Ala Met Gly His Ile Met Tyr Phe Arg Phe Ala Gln Asn
                    530                 535                 540
    Thr Leu Gly Asn Lys Leu Phe Ala Cys Gly Pro Asp Ala Lys Glu Val
    545                 550                 555                 560
    Arg Lys Glu Asn Gln Ala Asn Thr Ser Val Val
                    565                 570
```

```
<210> SEQ ID NO 5
<211> LENGTH: 19
<212> TYPE: DNA
<213> ORGANISM: Homo sapiens
<220> FEATURE:
<221> NAME/KEY: exon
<222> LOCATION: (1)..(19)

<400> SEQUENCE: 5 ccc cga ctc ggt ata aga g                                          19
Pro Arg Leu Gly Ile Arg
1               5

<210> SEQ ID NO 6
<211> LENGTH: 20
<212> TYPE: DNA
<213> ORGANISM: Homo sapiens
<220> FEATURE:
<221> NAME/KEY: exon
<222> LOCATION: (1)..(20)

<400> SEQUENCE: 6 ttc ctc cag aac tcg tgt ag                                         20
Phe Leu Gln Asn Ser Cys
1               5

<210> SEQ ID NO 7
<211> LENGTH: 20
<212> TYPE: DNA
<213> ORGANISM: Homo sapiens
<220> FEATURE:
<221> NAME/KEY: exon
<222> LOCATION: (1)..(20)

<400> SEQUENCE: 7 tgg ata agc att ctg ccc tc                                         20
Trp Ile Ser Ile Leu Pro
1               5
```

```
<210> SEQ ID NO 8
<211> LENGTH: 21
<212> TYPE: DNA
<213> ORGANISM: Homo sapiens
<220> FEATURE:
<221> NAME/KEY: exon
<222> LOCATION: (1)..(21)

<400> SEQUENCE: 8 taa agc atg tgt act tgg atg                                          21
    Ser Met Cys Thr Trp Met
    1               5

<210> SEQ ID NO 9
<211> LENGTH: 19
<212> TYPE: DNA
<213> ORGANISM: Homo sapiens
<220> FEATURE:
<221> NAME/KEY: exon
<222> LOCATION: (1)..(19)

<400> SEQUENCE: 9 aat gta gcc agg aag tgc c                                            19
Asn Val Ala Arg Lys Cys
1               5

<210> SEQ ID NO 10
<211> LENGTH: 19
<212> TYPE: DNA
<213> ORGANISM: Homo sapiens
<220> FEATURE:
<221> NAME/KEY: exon
<222> LOCATION: (1)..(19)

<400> SEQUENCE: 10 aga ggt ggt gcc atc taa g                                            19
Arg Gly Gly Ala Ile
1               5

<210> SEQ ID NO 11
<211> LENGTH: 20
<212> TYPE: DNA
<213> ORGANISM: Homo sapiens
<220> FEATURE:
<221> NAME/KEY: exon
<222> LOCATION: (1)..(20)

<400> SEQUENCE: 11 gga taa gaa cag tct cac tg                                           20
Gly     Glu Gln Ser His
1               5

<210> SEQ ID NO 12
<211> LENGTH: 21
<212> TYPE: DNA
<213> ORGANISM: Homo sapiens
<220> FEATURE:
<221> NAME/KEY: exon
<222> LOCATION: (1)..(21)

<400> SEQUENCE: 12 ttc atc ctt tac cac tac cag                                          21
Phe Ile Leu Tyr His Tyr Gln
1               5

<210> SEQ ID NO 13
<211> LENGTH: 20
```

```
<212> TYPE: DNA
<213> ORGANISM: Homo sapiens
<220> FEATURE:
<221> NAME/KEY: exon
<222> LOCATION: (1)..(20)

<400> SEQUENCE: 13 tta aac tgc ctt gtt tag tg                                           20
Leu Asn Cys Leu Val
1               5

<210> SEQ ID NO 14
<211> LENGTH: 19
<212> TYPE: DNA
<213> ORGANISM: Homo sapiens
<220> FEATURE:
<221> NAME/KEY: exon
<222> LOCATION: (1)..(19)

<400> SEQUENCE: 14 gcc tca ttt atc acc acc g                                            19
Ala Ser Phe Ile Thr Thr
1               5

<210> SEQ ID NO 15
<211> LENGTH: 20
<212> TYPE: DNA
<213> ORGANISM: Homo sapiens
<220> FEATURE:
<221> NAME/KEY: exon
<222> LOCATION: (1)..(20)

<400> SEQUENCE: 15 ttg tgt aaa tgg gca gtc tc                                           20
Leu Cys Lys Trp Ala Val
1               5

<210> SEQ ID NO 16
<211> LENGTH: 20
<212> TYPE: DNA
<213> ORGANISM: Homo sapiens
<220> FEATURE:
<221> NAME/KEY: exon
<222> LOCATION: (1)..(20)

<400> SEQUENCE: 16 cct cgt cta cca aag cga ta                                           20
Pro Arg Leu Pro Lys Arg
1               5

<210> SEQ ID NO 17
<211> LENGTH: 20
<212> TYPE: DNA
<213> ORGANISM: Homo sapiens
<220> FEATURE:
<221> NAME/KEY: exon
<222> LOCATION: (1)..(20)

<400> SEQUENCE: 17 gct ttt att tct aca tgt cc                                           20
Ala Phe Ile Ser Thr Cys
1               5

<210> SEQ ID NO 18
<211> LENGTH: 20
<212> TYPE: DNA
<213> ORGANISM: Homo sapiens
<220> FEATURE:
<221> NAME/KEY: exon
```

```
<222> LOCATION: (1)..(20)

<400> SEQUENCE: 18 gct gtg cca atc ctg aga tc                                          20
Ala Val Pro Ile Leu Arg
1               5

<210> SEQ ID NO 19
<211> LENGTH: 19
<212> TYPE: DNA
<213> ORGANISM: Homo sapiens
<220> FEATURE:
<221> NAME/KEY: exon
<222> LOCATION: (1)..(19)

<400> SEQUENCE: 19 gag cat cag cta taa ctg g                                           19
Glu His Gln Leu     Leu
1               5

<210> SEQ ID NO 20
<211> LENGTH: 21
<212> TYPE: DNA
<213> ORGANISM: Homo sapiens
<220> FEATURE:
<221> NAME/KEY: exon
<222> LOCATION: (1)..(21)

<400> SEQUENCE: 20 taa tgg att ctc tga acc tac                                         21
    Trp Ile Leu     Thr Tyr
        1               5

<210> SEQ ID NO 21
<211> LENGTH: 21
<212> TYPE: DNA
<213> ORGANISM: Homo sapiens
<220> FEATURE:
<221> NAME/KEY: exon
<222> LOCATION: (1)..(21)

<400> SEQUENCE: 21 ttg aaa tgt atg cct gta aac                                         21
Leu Lys Cys Met Pro Val Asn
1               5

<210> SEQ ID NO 22
<211> LENGTH: 21
<212> TYPE: DNA
<213> ORGANISM: Homo sapiens
<220> FEATURE:
<221> NAME/KEY: exon
<222> LOCATION: (1)..(21)

<400> SEQUENCE: 22 ttt cca tgc ctc aac ata agg                                         21
Phe Pro Cys Leu Asn Ile Arg
1               5

<210> SEQ ID NO 23
<211> LENGTH: 20
<212> TYPE: DNA
<213> ORGANISM: Homo sapiens
<220> FEATURE:
<221> NAME/KEY: exon
<222> LOCATION: (1)..(20)

<400> SEQUENCE: 23
```

```
gtt ttt acc aca gct gtg cc                                              20
Val Phe Thr Thr Ala Val
1               5

<210> SEQ ID NO 24
<211> LENGTH: 22
<212> TYPE: DNA
<213> ORGANISM: Homo sapiens
<220> FEATURE:
<221> NAME/KEY: exon
<222> LOCATION: (1)..(22)

<400> SEQUENCE: 24 ata cct taa gat caa tag gat c                                           22
Ile Pro     Asp Gln     Asp
1                       5

<210> SEQ ID NO 25
<211> LENGTH: 15
<212> TYPE: DNA
<213> ORGANISM: Homo sapiens
<220> FEATURE:
<221> NAME/KEY: N_region
<222> LOCATION: (7)..(9)

<400> SEQUENCE: 25
tattgcaaat ttggc                                                        15

<210> SEQ ID NO 26
<211> LENGTH: 15
<212> TYPE: DNA
<213> ORGANISM: Homo sapiens
<220> FEATURE:
<221> NAME/KEY: mutation
<222> LOCATION: (7)..(9)

<400> SEQUENCE: 26
tattgcacat ttggc                                                        15
```